United States Patent [19]

Kitson et al.

[11] 4,196,245
[45] Apr. 1, 1980

[54] COMPOSITE NONWOVEN FABRIC COMPRISING ADJACENT MICROFINE FIBERS IN LAYERS

[75] Inventors: Richard P. Kitson, Germantown; Richard L. Gilbert, Jr.; Joseph Israel, both of Memphis, all of Tenn.

[73] Assignee: Buckeye Cellulos Corporation, Memphis, Tenn.

[21] Appl. No.: 915,913

[22] Filed: Jun. 16, 1978

[51] Int. Cl.$^2$ .............................................. B32B 7/14
[52] U.S. Cl. ........................... 428/198; 2/DIG. 7; 428/284; 428/287; 428/297; 428/302; 428/903
[58] Field of Search ............... 428/198, 284, 287, 297, 428/302, 903; 2/DIG. 7

[56] References Cited

U.S. PATENT DOCUMENTS

| | | | |
|---|---|---|---|
| 3,169,899 | 2/1965 | Steuber | 428/198 |
| 3,485,706 | 12/1969 | Evans et al. | 428/134 |
| 3,597,299 | 8/1971 | Thomas et al. | 428/108 |
| 3,602,220 | 8/1971 | Bunyon | 128/156 |
| 3,639,199 | 2/1972 | Brandts et al. | 128/284 |
| 3,770,562 | 11/1973 | Newman | 156/313 |
| 3,788,936 | 1/1974 | Brock et al. | 428/152 |
| 3,824,997 | 7/1974 | Franklin | 128/156 |
| 3,837,995 | 9/1974 | Floden | 428/296 |
| 3,862,877 | 1/1975 | Camden | 128/290 W |
| 3,890,974 | 6/1975 | Kozak | 128/287 |
| 3,929,135 | 12/1975 | Thompson | 128/287 |
| 3,932,682 | 1/1976 | Loft et al. | 428/296 |
| 3,989,867 | 11/1976 | Sisson | 428/132 |
| 4,041,203 | 8/1977 | Brock et al. | 428/157 |

*Primary Examiner*—James J. Bell
*Attorney, Agent, or Firm*—Frost & Jacobs

[57] ABSTRACT

A composite nonwoven fabric for use in disposable surgical items such as surgical gowns, surgical drapes and the like. The fabric comprises at least two hydrophobic piles of microfine fibers of a fiber diameter of up to about 10 microns and at least one nonwoven cover ply. The nonwoven cover ply may be an apertured film, a spunbonded ply or an air laid, wet laid or carded ply of fibers preferably of staple length or longer. The cover ply may lend strength to the fabric and, of particular importance to surgical items, should be characterized by surface stability. When a single cover ply is employed, the exposed melt blown ply should be surface stabilized to improve its resistance to abrasion and pilling. When additional strength is required, the fabric may include a strength ply of hydrophobic spunbonded, air laid, wet laid or carded fibers. The composite nonwoven fabric demonstrates a unique relationship between air permeability and resistance to liquid and bacterial strikethrough, while maintaining cloth-like aesthetics substantially equivalent to those normally associated with woven fabrics.

36 Claims, 11 Drawing Figures

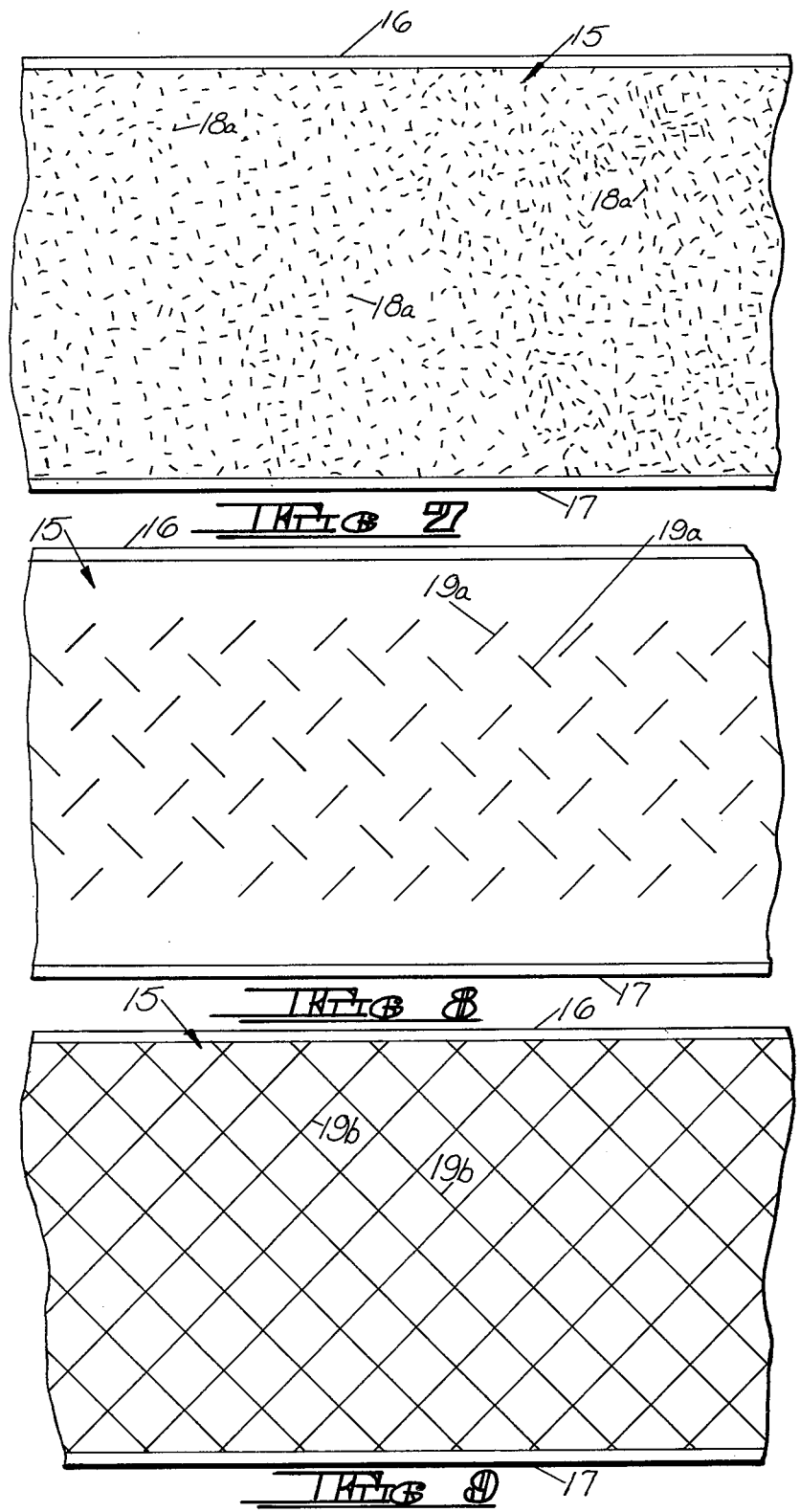

COMPOSITE NONWOVEN FABRIC COMPRISING ADJACENT MICROFINE FIBERS IN LAYERS

BACKGROUND OF THE INVENTION

1. Field of the Invention

The invention relates to a composite nonwoven fabric and more particularly to such a fabric which is characterized by unique relationships between air permeability and resistance to liquid and bacteria strikethrough.

2. Description of the Prior Art

The composite nonwoven fabric of the present invention has many applications and, in fact, may be used wherever its unique liquid or bacteria strikethrough resistance/air permeability relationships would be advantageous. For example, the fabric could be used in the manufacture of laboratory coats, artist's smocks, hospital scrub clothes, rain wear or the like. As used herein and in the claims, the phrases "liquid strike-through" and "bacteria strikethrough" refer respectively to the passage of liquid or bacteria from one surface of the fabric, through the fabric, to the other surface of the fabric.

While not intended to be so limited, the composite nonwoven fabric of the present invention will be described primarily in terms of its application to surgical items such as surgical gowns, surgical drapes and the like. The choice to so describe the composite nonwoven fabric has been made for two reasons. First of all, the fabric of the present invention lends itself particularly well to surgical applications, and secondly, the requirements for surgical applications are generally far more stringent than those for other applications.

Prior art workers have developed a number of fabrics for use in surgical gowns, surgical drapes and the like. There are a number of critical physical properties which are sought for such fabrics. These properties include: essentially no particulate discharge (lint or the like), essentially no abrasion or pilling, high liquid strikethrough resistance, high bacteria strikethrough resistance, adequate strength and tear resistance, surface conductivity (i.e. a surface which will not hold a static charge which would be dangerous in the presence of explosive anesthetic and the like), an anti-glare surface, flame retardancy, and a cloth like aesthetic primarily consisting of quietness and good hand (including such attributes as drape, feel, and flexibility). Exemplary prior art fabrics are taught in U.S. Pat. No. 3,837,995 in the name of John G. Floden, issued Sept. 24, 1974 and U.S. Pat. No. 4,041,203 in the names of Robert J. Brock and Gary H. Meitner, issued Aug. 9, 1977.

While prior art workers have been able to achieve a number of these physical properties with a high degree of success, historically a single fabric (whether intended for reuseable or disposable surgical items) has not been developed which possesses all of these physical properties simultaneously. It has hitherto been necessary to aim for the best possible trade-off between some at least of these properties. This is true, in part, because some of these properties tend to work against each other. A good example of this is air permeability on the one hand and liquid strikethrough resistance on the other. Prior art workers have devised nonwoven materials such as a flashspun polyolefin material (as taught in U.S. Pat. No. 3,169,899 in the name of Walter Steuber, issued Feb. 16, 1965) for disposable surgical gowns and drapes, and tightly woven waterproofed pima cotton fabrics for reusable surgical gowns and drapes. While these materials demonstrate good liquid strikethrough resistance (in the neighborhood of from 600 to 1000 millimeters of $H_2O$), they demonstrate relatively low air permeability (i.e. below about 25 $mm^3$/sec-$mm^2$ at 12.7 mm $H_2O$ differential pressure).

Other nonwoven fabrics have been developed for use in disposable surgical gowns and drapes. One such fabric comprises three or four tissue plies reinforced with a nylon or cotton scrim. A fabric comprising a spunbonded web saturated with a suitable binder such as an acrylic latex and located between soft, absorbent tissue facing layers is taught in copending application Ser. No. 741,640, filed Nov. 15, 1976 in the names of Larry L. Lafitte and James B. Camden and entitled QUIET, STRONG CLOTH-LIKE TISSUE LAMINATE. Yet another example comprises hydraulically entangled polyester and wood pulp tissue webs, as described in U.S. Pat. No. 3,485,706 in the name of Franklin J. Evans, issued Dec. 23, 1969. These last mentioned nonwovens demonstrate air permeabilities ranging from about 50 to about 500 $mm^3$/sec-$mm^2$ at 12.7 mm $H_2O$ differential pressure. They also demonstrate liquid strikethrough values of 250 mm of $H_2O$ or less.

The present invention is directed to a composite nonwoven fabric having a liquid strikethrough resistance/air permeability relationship far superior to any hitherto known. The composite nonwoven fabric simultaneously demonstrates an air permeability in excess of 100 $mm^3$/sec-$mm^2$ and preferably in excess of 150 $mm^3$/sec-$mm^2$ at 12.7 mm $H_2O$ differential pressure and a liquid strikethrough resistance well in excess of 250 mm of $H_2O$, as will be shown hereinafter. In addition, the nonwoven, composite fabric of the present invention is capable of resisting liquid strikethrough when subjected to pressure between two opposed surfaces far better than even those surgical fabrics which demonstrate higher liquid column strikethrough resistances. This is also true when the fabric is subjected to such opposed pressure repeatedly. This property is significant since most pressures to which surgical fabrics are subjected in the operating room are of the opposed type, as for example the sleeve of a surgical gown when the surgeon leans his forearm against the patient or some other object.

Bacteria strikethrough resistance is the primary purpose of a surgical gown or drape. Heretofore it has been generally accepted that the liquid column strikethrough resistance of a surgical fabric is a measure of its bacteria strikethrough resistance, since liquids are the primary carriers of bacteria. This, however, does not take into account other possible modes of bacteria transmission and the fact that most pressures to which surgical fabrics are subjected in the operating room are of the opposed type. The composite nonwoven fabric of the present invention demonstrates superior bacteria strikethrough resistance, when measured directly and under pressure from opposed surfaces, as will be described hereinafter. Thus the fabric of the present invention exhibits not only a unique air permeability/liquid strikethrough resistance relationship, but also a unique air permeability/bacteria strikethrough resistance relationship as well.

In addition, the fabric is sufficiently tough and tear resistant for surgical use and can readily be treated to be flame retardant and surface conductive, when required. The fabric has surfaces which are essentially free of particle discharge, highly resistant to abrasion or pilling and appropriately colored so as to be free of glare. The fabric achieves a high degree of cloth-like character including quietness and good hand.

SUMMARY OF THE INVENTION

The present invention is directed to a composite nonwoven fabric which, although not so limited, is particularly suited for use in disposable surgical items such as surgical gowns, surgical drapes and the like. In its simplest embodiment, the composite nonwoven fabric comprises at least two hydrophobic plies of microfine fibers of a fiber diameter of about 10 microns or less and a cover ply adjacent one of the plies of microfine fibers. The cover ply may lend strength to the fabric and, particularly when the fabric is intended for use in surgical items, should be characterized by surface stability, i.e. resistance to abrasion and pilling. When a single cover ply is employed, the exposed microfine fiber ply should be stabilized to improve its resistance to abrasion and pilling.

The cover ply may be an apertured film, a spunbonded web of rayon, polyester, polypropylene, nylon, or blends thereof, or a discontinuous fiber web comprising an air laid, wet laid or carded web preferably of staple length or longer fibers made from cellulose (such as cotton), rayon, synthetic material (such as polypropylene, polyester or nylon) or mixtures thereof. A tissue web may also be used.

Another basic embodiment of the present invention differs from that described above only in that it is provided with two cover plies. The cover plies may be selected from any of the apertured film, spunbonded, webs or discontinuous fiber webs mentioned above. The cover plies may be identical or dissimilar depending upon the particular surface properties sought for the fabric, as will be described hereinafter.

In both of the embodiments described above, there must be at least two hydrophobic plies of microfine fibers. There may be more than two such plies. In general, little advantage will be achieved if the number of such plies exceeds about 4 or 5. The number of microfine fiber plies will depend upon such factors as the nature of the cover plies, the basis weight and uniformity of the microfine fiber plies and cost.

In both of the embodiments mentioned above, if the one or two cover plies do not impart sufficient strength to the fabric to meet the particular requirement of the use to which the fabric is put, an additional internal strength ply may be incorporated in the fabric. Such a strength ply may comprise any one of the above mentioned spunbonded or discontinuous fiber webs. Such a strength web should be hydrophobic in nature and may be located anywhere within the fabric structure, so long as it will not interfere with appropriate bonding of the fabric plies, as will be described hereinafter.

In both embodiments, the two or more microfine fiber plies, and preferably the entire fabric structure, should be unbonded or minimally bonded to assure achievement of the unique liquid and bacteria strikethrough resistance/air permeability relationships of the fabric. To this end, the plies of the fabric are preferably joined only at the edges of the fabric or at the seams of the gown, drape or other structure made of the fabric. In instances where additional joining of the plies is desirable, spot bonding, as is well known in the art, may be employed. Bonding may be accomplished by the use of an appropriate bonding agent preferably a hydrophobic bonding agent. Heat bonding may also be employed.

BRIEF DESCRIPTION OF THE DRAWINGS

FIG. 7 is a fragmentary plan view similar to FIG. 6 and illustrating random point bonding.

FIG. 8 is a fragmentary plan view similar to FIG. 6 and illustrating discontinuous pattern bonding.

FIG. 9 is a fragmentary plan view similar to FIG. 6 and illustrating continuous pattern bonding.

DESCRIPTION OF THE PREFERRED EMBODIMENT

Figure 1:
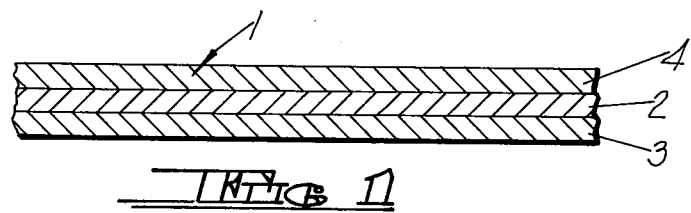
FIG. 1 is a semi-diagrammatic, fragmentary, cross sectional view of one embodiment of the fabric of the present invention.

One embodiment of the fabric of the present invention is illustrated in FIG. 1, which constitutes a semi-diagrammatic cross sectional view. The embodiment of FIG. 1, generally indicated at 1, comprises a three-ply structure. It will be understood that the plies have been exaggerated in thickness for purposes of clarity.

Plies 2 and 3 each comprise a nonwoven web of microfine hydrophobic fibers having a fiber diameter of up to about 10 microns and preferably up to about 4 microns. For example, plies 2 and 3 may be melt-blown plies of the type taught in the article entitled SUPERFINE THERMOPLASTIC FIBERS by Van A. Wente, appearing in INDUSTRIAL ENGINEERING CHEMISTRY, August, 1956, Volume 48, No. 8 (pp. 1342–1346). While the melt-blown material may be nylon, polyester, or any polymer or polymer blend capable of being melt-blown, a melt-blown polypropylene web is preferred. Each of plies 2 and 3 could comprise 2 or more layers or zones of different melt-blown polymers. Plies 2 and 3 each should have a basis weight of at least about 10 g/m$^2$ and preferably a basis weight of from about 15 g/m$^2$ to about 30 g/m$^2$, and a density of up to about 0.15 g/cc and preferably up to about 0.1 g/cc. Plies 2 and 3 may or may not be identical.

The embodiment of FIG. 1 has a cover ply 4. As will be evident hereinafter, selection of the cover ply 4 should be made in accordance with the properties required of the surface of the fabric, depending upon the intended use of the fabric. For purposes of this invention, the cover ply 4 should be air permeable and, when intended for use in surgical drapes or gowns, should be characterized by essentially no lint discharge and high resistance to abrasion and pilling. The cover ply should be treatable either during its manufacture or thereafter so as to have good surface conductivity and to be flame retardant, if required. It should be capable of being colored in such a fashion as to be free of glare.

Figure 2:
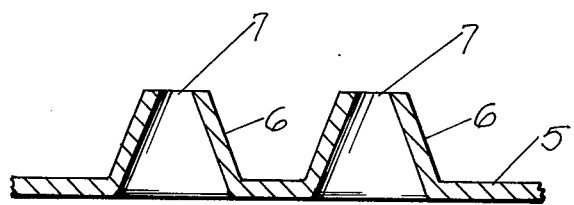
FIG. 2 is a fragmentary cross sectional view of an exemplary apertured film.

The cover ply 4 may, for example, constitute an apertured film of the type described in U.S. Pat. No. 3,929,135 in the name of Hugh Ansley Thompson and dated Dec. 30, 1975 and U.S. Pat. No. 3,989,867 in the name of James Bryant Sisson and dated Nov. 2, 1976. These references teach the formation in a liquid impervious film of a plurality of tapered capillaries, each with its base in the plane of the film or a portion thereof and its apex remote therefrom. An exemplary film of this type is illustrated at 5 in FIG. 2. The film 5 is shown having a plurality of capillaries in the form of cones 6 formed therein. Each cone tapers upwardly and inwardly and terminates in an opening 7. The film 5 preferably has a thickness of from about 0.01 mm to about 0.05 mm before the formation of the cones 6. The film may be any appropriate flexible, liquid impervious film which is embossable. The film is preferably a thermoplastic such as polyethylene or the like.

Apertured film of the type just described constitutes a preferred cover ply for many surgical applications for a number of reasons. The apertured film is air permeable and can be naturally hydrophobic. It is abrasion resistant and lint free. The film is opaque and can be easily and economically obtained in a range of non-glare colors. It can readily be rendered electrically conductive either by adding an anti-static agent to the polymer prior to film formation, or by treating the completed film with an anti-static agent, as is known in the art. It can similarly be rendered flame retardant.

In the above mentioned U.S. Pat. Nos. 3,929,135, and 3,989,867 the apertured film is taught as being a surface layer for absorptive devices such as diapers, sanitary napkins, bed pads, incontinent pads, towels, bandages and the like. Under these circumstances it is preferred that the cones 6 be so oriented as to face inwardly toward the inner absorptive layers of the structure. In the present application, when the apertured film serves as the single cover ply 4 of the structure of FIG. 1, it is preferred that the cones extend upwardly of the fabric surface, i.e. away from plies 2 and 3. This orientation of the apertured film promotes both the bacteria strikethrough resistance and liquid strikethrough resistance of the fabric. Thus, when the exterior surface of apertured film is subjected to a liquid, the liquid tends to collect between the cones 6. When the fabric is subject to pressure by opposed surfaces, the cones 6 tend to crush, partially or completely closing the apertures 7.

The cover ply 4 may also constitute a spunbonded web having a basis weight of up to about 34 g/m$^2$. When a spunbonded web is used as cover ply 4, it should constitute a continuous filament web having a filament diameter of up to about 40 microns. The spunbonded material may be made from any polymer or polymer blend capable of being spunbonded, the most common being rayon, polyester, polypropylene or nylon. Spunbonded polymers such as polyester, polypropylene and nylon are naturally hydrophobic. Spunbonded polymers such as rayon are naturally hydrophilic and may be used when it is desired that cover ply 4 be an absorptive cover ply, or may be treated to be hydrophobic, as is well known in the art. The spunbonded web may comprise two or more layers of different polymers or polymer blends.

Since spunbonded webs are by virtue of their manufacturing process continuous filament webs, they are naturally strong, abrasion resistant and lint free. Such webs can be appropriately colored and can be treated to be surface conductive and flame retardant if required.

The cover ply 4 may also be made of nonwoven webs of discontinuous fibers such as tissue. To achieve a good balance of abrasion resistance, air permeability and low lint discharge it is desirable that the fibers be of substantially staple length or longer (i.e. about 10 mm or more). Such webs may, for example be wet laid, air laid or carded webs of cellulose fibers (such as cotton), rayon fibers, synthetic fibers such as polypropylene, polyester or nylon fibers, or mixtures or layers of cellulose or rayon and synthetic fibers.

While such discontinuous fiber cover plies perform well, they are generally less strong then spunbonded cover plies. Again, the discontinuous fiber plies should have a basis weight of up to about 34 g/m$^2$. These plies can also be appropriately colored and can be treated with an anti-static agent and a flame retardant agent, as is well known in the art.

In the embodiment of FIG. 1, the microfine fiber ply 3 is exposed (i.e. not protected by a cover ply). Under these circumstances it is desirable to surface stabilize ply 3 to improve its abrasion resistance. This can be accomplished in a number of well known ways, as by heat embossing the ply. Such surface stabilization will increase the density of ply 3 detracting somewhat from the liquid and bacteria strikethrough resistance/air permeability relationships.

Figure 3:
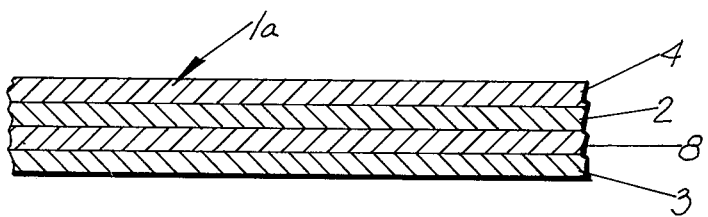
FIG. 3 is a semi-diagrammatic, fragmentary, cross sectional view of the embodiment of FIG. 1 provided with an internal strength ply.

The fabric of FIG. 1, as a whole, should be sufficiently strong to efficiently serve the purpose for which it is intended. If the fabric does not have sufficient strength, it may include at least one additional internal strength ply. FIG. 3 illustrates a fabric 1a substantially identical to that of FIG. 1 and like parts have been given like index numerals. The embodiment of FIG. 3 differs from that of FIG. 1 in that it includes a strength ply 8. The strength ply 8 may constitute any one of the spunbonded, or discontinuous fiber webs described above with respect to cover ply 4, with the exception that it must be naturally hydrophobic or treated to be hydrophobic. The strength ply 8, is illustrated as being located between the microfine fiber plies 2 and 3. It may also be located between the microfine fiber ply 2 and cover ply 4, so long as the strength ply 8 and cover ply 4 are of such nature that they will not interfere with the bonding of the fabric, as will be discussed hereinafter.

Figure 4:
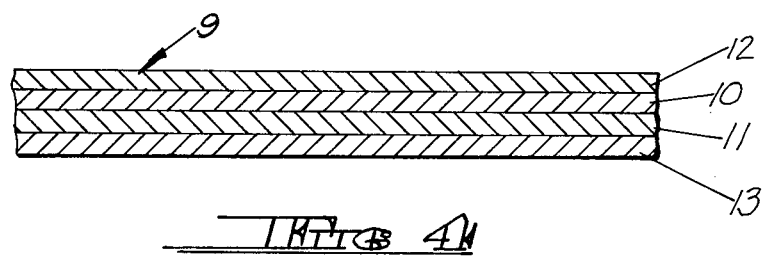
FIG. 4 is a semi-diagrammatic, fragmentary, cross sectional view of another embodiment of the fabric of the present invention provided with two cover plies.

Another fabric embodiment of the present invention is illustrated in FIG. 4 and is generally indicated at 9. The fabric of FIG. 4 comprises a pair of microfine fiber webs 10 and 11, identical to the webs 2 and 3 described with respect to FIG. 1, with the exception that neither is exposed and thus requires no surface stabilization. The fabric 9 differs from the fabric 1 of FIG. 1 primarily in that it is provided with a pair of cover plies 12 and 13. Cover ply 12 is equivalent to cover ply 4 of FIG. 1. Cover ply 13 constitutes an additional cover ply. The cover plies 12 and 13 may be made of any of the materials described with respect to cover ply 4 of FIG. 1 including the apertured film, the spunbonded webs and the discontinuous fiber webs mentioned above. Cover plies 12 and 13 may be identical, or they may be dissimilar.

Figure 5:
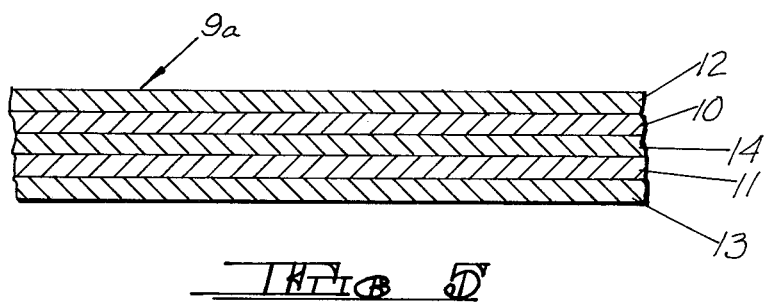
FIG. 5 is a semi-diagrammatic, fragmentary, cross sectional view of a fabric similar to that of FIG. 4, but provided with three microfine fiber layers.

In order to achieve the unique air permeability/liquid and bacteria strikethrough resistance relationships of the fabric of the present invention, it is necessary that the fabric contain at least two microfine fiber plies of the type described. It has been determined, for example, that two microfine fiber plies demonstrate greater liquid strikethrough resistance than a single microfine fiber ply having an equivalent basis weight. The fabric may contain more than two such plies as is illustrated in FIG. 5. FIG. 5 shows a fabric 9a similar to the fabric 9 of FIG. 4 and again like parts have been given like index numerals. The fabric 9a of FIG. 5 differs from the fabric 9 of FIG. 4 only in that a third microfine fiber ply 14 is provided. The third microfine fiber ply 14 may be identical or different from the plies 10 and 11, in the same manner as described with respect to plies 2 and 3 of FIG. 1.

The number of plies of mirofine fibers provided in the fabric will depend upon a number of factors including the severity of the conditions promoting liquid and bacteria strikethrough to which the fabric is subjected, the basis weight and uniformity of the microfine fiber plies, the nature of the one or more cover plies and cost. It has been found that when the number of microfine fiber plies exceeds more than about 4 or 5, the added advantage in liquid and bacteria strikethrough resistance is not great and will be offset by a diminished air permeability and impairment of the hand characteristics of the fabric including drape, conformability, lack of stiffness and the like.

In either of the fabrics of FIGS. 4 and 5, at least one internal strength ply may be included, if required. Such a strength ply should be the same as strength ply 8 described with respect to FIG. 3. The strength ply should be hydrophobic and may be located anywhere within the fabric structure so long as it does not interfere with the bonding of the structure.

In all of the fabric structures thus far described, it has been found that the entire structure should be only minimally bonded to assure achievement of the liquid and bacteria strikethrough/air porosity relationships mentioned above. To this end, the various plies of the fabric may be joined together only at the edges of the fabric or at the seams of a structure made of the fabric. When additional bonding is required to prevent the plies from slipping or shifting with respect to each other, spot bonding may be employed. The term "spot bonding" as used herein and in the claims is intended to be inclusive of continuous or discontinuous pattern bonding, uniform or random point bonding, or combinations thereof, all as are well known in the art.

Figure 6:
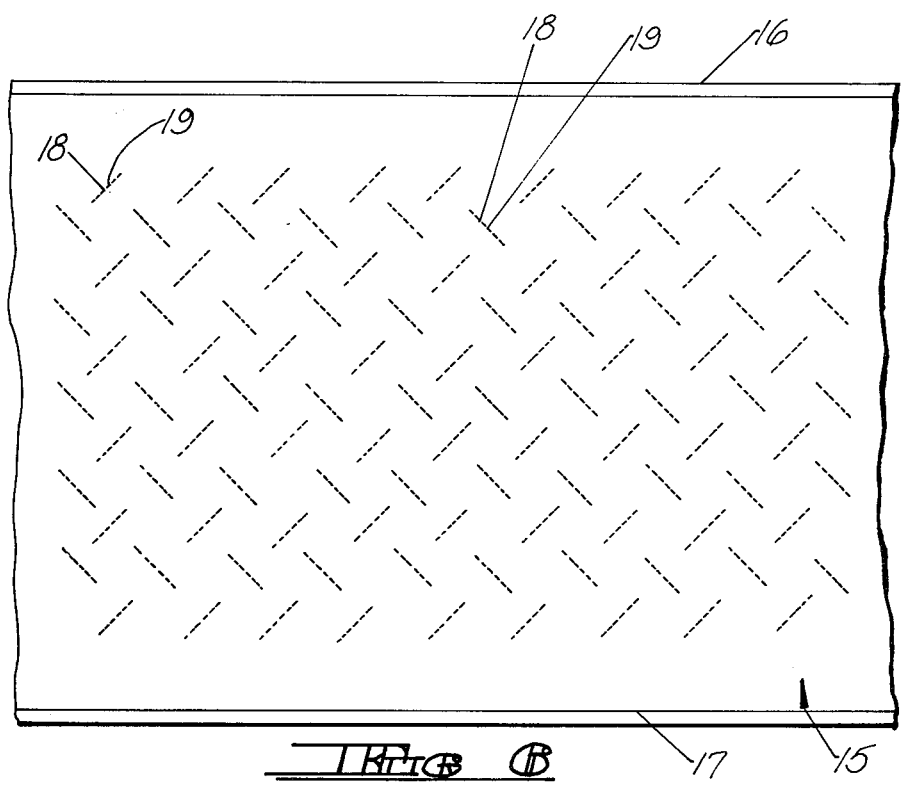
FIG. 6 is a fragmentary plan view of the fabric of the present invention illustrating both edge bonding and patterned point bonding.

Reference is made to FIG. 6 wherein a fabric of the present invention (which may be any of the fabrics illustrated in FIGS. 1 and 3 through 5) is fragmentarily shown. The fabric is generally indicated at 15. The fabric is illustrated as being joined along its peripheral edges as at 16, and 17. The fabric is further illustrated as being uniformly point bonded by individual point bonds 18 arranged in rows 19. The rows 19, in turn, are arranged in a decorative "chevron" pattern. FIG. 7 is similar to FIG. 6 and like parts have been given like index numerals. FIG. 7 differs from FIG. 6 in that it illustrates random point bonding, the point bonds 18a being randomly located on the fabric. In addition, point bonds 18a may or may not be randomly sized. FIG. 8 is again similar to FIG. 6 with like parts having been given like index numerals. FIG. 8 illustrates an exemplary form of discontinuous pattern bonding. The bonds 19a are similar to the rows 19 of FIG. 6, but themselves constitute continuous bond lines rather than a plurality of aligned point bonds. FIG. 9 (again similar to FIG. 6) depicts an example of continous pattern bonding wherein the stripes of bonding 19b extend continuously across the fabric. It will be understood that stripes 19b could extend in any direction including the machine or cross direction. It will further be understood that combinations of these various types of bonding could also be used.

It will be understood by one skilled in the art that at each individual bond position the fabric structure is stiffened and its air permeability is reduced or eliminated. Nevertheless, when appropriately designed and positioned, the bonds will cause no appreciable effect on the hand of the overall fabric structure and no significant effect on its liquid and bacteria strikethrough resistance/air permeability relationships. Both the edge bonds 16 and 17, the individual point, line or stripe bonds 18, 18a, 19a, and 19b can be accomplished in a number of ways. For example, they may be achieved by various well known methods of heat bonding including ultrasonic welding. All of the plies heretofore described are heat bondable with the exception of webs which are made up of 50% or more rayon fibers. Even when such webs are used as cover plies, heat bonding may be utilized since the adjacent thermoplastic webs will melt into and bond with such webs. The same is, of course, true of a 50% or more rayon fiber strength ply. However, it will be understood that such a strength ply should not be located adjacent a 50% or more rayon fiber cover ply, if heat bonding is to be used.

It is also possible to accomplish the edge bonds 16 and 17 and/or the point, line or stripe bonds 18, 18a, 19a and 19b through the use of any appropriate hydrophobic bonding agent. Such hydrophobic bonding agents are numerous, readily available and their uses are well known in the art. For example, the most commonly used bonding agents are acrylic latexes, styrene butadiene copolymers, ethylene vinyl acetate copolymers or a hot melt such as polyethylene.

The edge bonds 16 and 17 will incorporate all of the fabric plies. The same would be true at a seam in a structure made of the fabric. The individual spot, line or stripe bonds 18, 18a, 19a and 19b may be made after assembly of the fabric so as to join all of the plies or they may be used to join only selected ones of the fabric plies prior to final assembly of the fabric. For examle in the structures of FIGS. 1 and 3 through 5 such spot, line or stripe bonds can be used to join at least one outer ply to its adjacent inner ply. Two or more inner plies can also be bonded together. Various plies can be bonded by different bonding agents in different bonding patterns. Overall fabric bonding can also be used in conjunction with individual layer bonding.

As will be pointed out hereinafter, the fabrics of the present invention (as illustrated in FIGS. 1 and 3 through 5) demonstrate excellent air permeability well in excess of 100 mm$^3$/sec-mm$^2$ and preferably in excess of 150 mm$^3$/sec-mm$^2$ at 12.7 mm H$_2$O differential pressure and at the same time a liquid column strikethrough resistance well in excess of 250 mm H$_2$O and a bacteria strikethrough resistance in excess of 20 kilonewtons per square meter, as will be described hereinafter. The precise reason or reasons for the high liquid and bacteria strikethrough resistance characteristics of the fabric of the present invention are not fully known. Without wishing to be bound by theory, it is believed that there are several factors contributing to these properties of the fabrics. First of all, the at least two interior microfine fiber plies are not readily penetrated by liquid by virtue of their physical construction. In addition, these plies are hydrophobic. Beyond this, since these microfine fiber layers are unbonded or minimally bonded, a liquid penetrating one of these plies may have a tendency to spread laterally between that ply and the next before beginning to penetrate the next ply. Thus, there would be a pressure release between the plies of the microfine fibers. The same pressure release would occur between a microfine fiber ply and an adjacent strength ply or an adjacent hydrophobic cover ply. That is, this pressure release would occur between any two adjacent hydrophobic plies.

It is believed that the best liquid and bacteria strikethrough resistance/air permeability relationships are achieved when one or both of the cover plies constitute apertured film of the type described above. As indicated above liquid on the exterior of the fabric tends to collect between the cones of the apertured film ply. In addition, the cones tend to collapse when the fabric is subjected to pressure by opposed surfaces, thus partially or completely closing the apertures in the cones. It has additionally been found that when the fabric is provided with two cover plies, both of apertured film, the orientation of the cones (facing outwardly or facing inwardly of the center plies) does not make as significant a difference as when only a single apertured film cover ply is used. In either event, however, orienting the apertured film in such a way that the cones face outwardly of the fabric is preferred.

It has further been determined that the use of at least one cover ply which is hydrophilic (i.e. absorbent in nature) does not materially effect either the high bacteria strikethrough resistance or the high liquid strikethrough resistance characteristics of the fabrics of the present invention. There may be instances where it would be desirable to provide an absorbent cover ply (such as a spun-bonded rayon ply). For example, an absorbent ply may be provided on that surface of a garment which is adjacent the wearer's skin. Such a ply would not only be comfortable, but also would tend to absorb perspiration.

The fabrics of the present invention are characterized by excellent hand properties inclusive of drape, feel, conformability or flexibility, and compressibility. In addition, these fabrics are quiet, lacking the paper-like crinkle or rattle which is characteristic of most prior art nonwoven surgical fabrics.

The fabrics of the present invention afford a unique versatility in the manner in which they may be made up to meet the particular requirements of the use for which they are intended. For an exemplary illustration of this versatility, reference is made to FIG. 10 which illustrates a typical surgical gown generally indicated at 20. The gown comprises sleeves 21 and 22 which may be provided with cuffs 23 and 24, respectively. The gown has a front panel 25 which is intended to cover the front portion of the surgeon and to extend partially around his sides. A pair of rear panels 26 and 27 are intended to extend behind the surgeon and will normally overlap. Means (not shown) may be provided to belt and tie the gown.

The fabrics of the present invention lend themselves well to use in such surgical gowns. This is true not only because of their cloth-like characteristics and their surface conductivity, anti-glare and flame retardant properties, but also because of their unique air permeability/liquid and bacteria strikethrough resistance relationships. The fact that the fabrics are air permeable will contribute greatly to the surgeon's comfort. The fabrics high resistance to bacteria and liquid strikethrough is of great importance to both the patient's and the surgeon's safety.

The gown may be made entirely of any one of the above described fabric embodiments. The exterior surface of the gown should be hydrophobic as well as being appropriately colored and electrically conductive. The plies of the fabric from which the gown is made may be bonded together only at sleeve seams 28 and 29, seams 30 and 31 where the sleeves join the gown, seams 32 and 33 were the front panel 25 joins back panels 26 and 27 and at the peripheral edges of the gown. Where additional bonding of the fabric is deemed desirable, any of the methods described above may be employed.

It is possible to make various parts of the surgical gown 20 from various ones of the fabric embodiments of the present invention to best meet the needs of that particular gown part. For example, the sleeves 21 and 22 of the gown constitute portions of the gown most likely to be subjected to opposed pressure and therefore are most likely to suffer from liquid and bacteria strikethrough. They also constitute the only part of the gown which normally has direct contact with the surgeon's skin since most scrub cloths are short sleeved. As a result, in an exemplary preferred embodiment the sleeves may be made of a composite nonwoven fabric comprising an outer cover ply of apertured film (with its cones extending outwardly of the fabric), three microfine fiber plies and an inner cover ply to lend strength to the fabric and to be comfortable against the surgeon's skin. Such a comfort ply can comprise a spun-bonded or a discontinuous fiber web of rayon. Such webs are naturally hydrophilic and thus would be absorbent. If desired, they could be treaed to be hydrophobic.

The next most critical portion of the gown is the front panel 25 and, in particular, the upper portion of that panel defined by the surgeon's neck, shoulders and waist. An exemplary front panel would comprise an apertured film outer cover ply, two hydrophobic microfine fiber plies and an inner cover ply either of apertured film or in the form of a comfort ply of the type described above.

The back panels 26 and 27, while they should be comfortable and air permeable are far less likely to be subjected to liquids or bacteria. As a consequence, back panels 26 and 27 could be made up of any appropriate nonwoven fabric. They could, for example, be made up of a fabric simply comprising an apertured film outer ply and a single microfine fiber ply suitably stabilized.

Surgical gowns of the type described could be made up of fabrics tailored to the nature of the operation to be performed. For example, the number of plies and their nature could be varied depending upon the amount of medical and body liquids likely to be encountered by the surgical gown by virtue of the nature of the operation to be performed.

Figure 11:
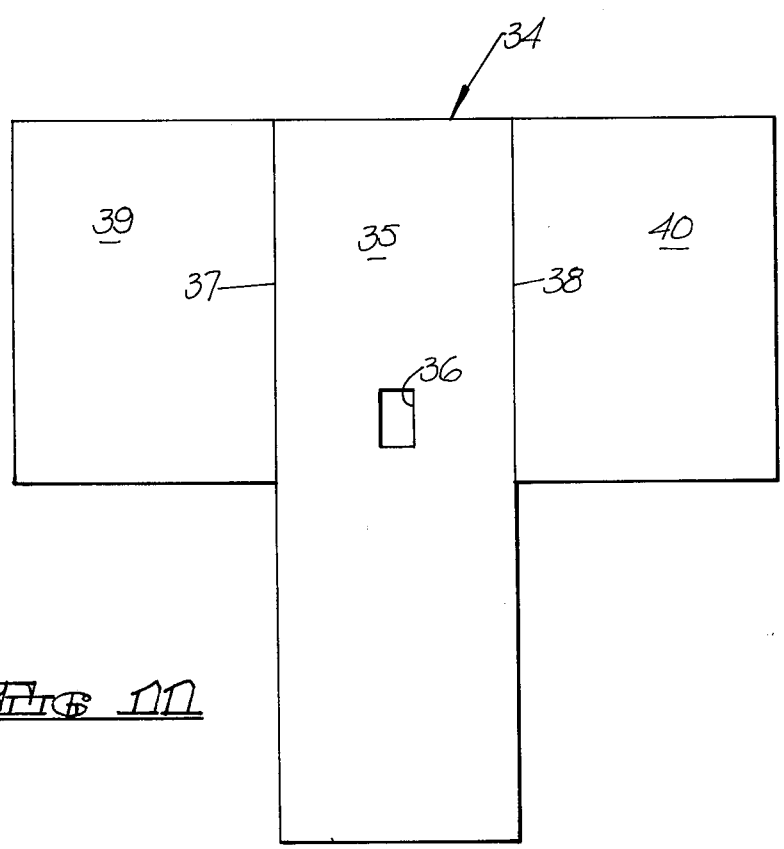
FIG. 11 is a plan view of an exemplary surgical drape made of the fabric of the present invention.

FIG. 11 illustrates an exemplary surgical drape. The drape has a main portion 35 provided with a fenestration 36 at the site of the surgery. Connected to the main body portion 35 at seams 37 and 38 there may be additional panels 39 and 40 adapted to cover the sides of the patient and extend downwardly over the edges of the operating table.

Again the surgical drape 34 may be made up of any of the fabric embodiments of the present invention. The fabric plies may be joined together only along the seams 37 and 38 and along the peripheral edges of the drape.

The plies may be additionally bonded, as described above, if desired. While the drape 34 may be provided with an upper or outer cover ply selected from any of the above taught cover plies which are hydrophobic in nature, in many instances it is desirable to have an absorbent upper cover ply to control liquid run-off. To this end, an exemplary construction of the drape 34 comprises an upper cover ply of spunbonded rayon or a web of discontinuous fibers of 100% rayon or a mixture of rayon fibers and synthetic fibers such as polypropylene, polyester or nylon fibers. The drape 34 may also be provided with two or more hydrophobic microfine fiber layers, the bottommost one of which is surface stabilized to improve its abrasion resistance. Thus, the drape may have a construction similar to that illustrated in FIG. 1.

The drape could also be provided with an inner cover ply, as for example an apertured film cover ply. The innermost cover ply need not constitute a comfort ply particularly in instances where the patient is anesthetized.

Figure 10:
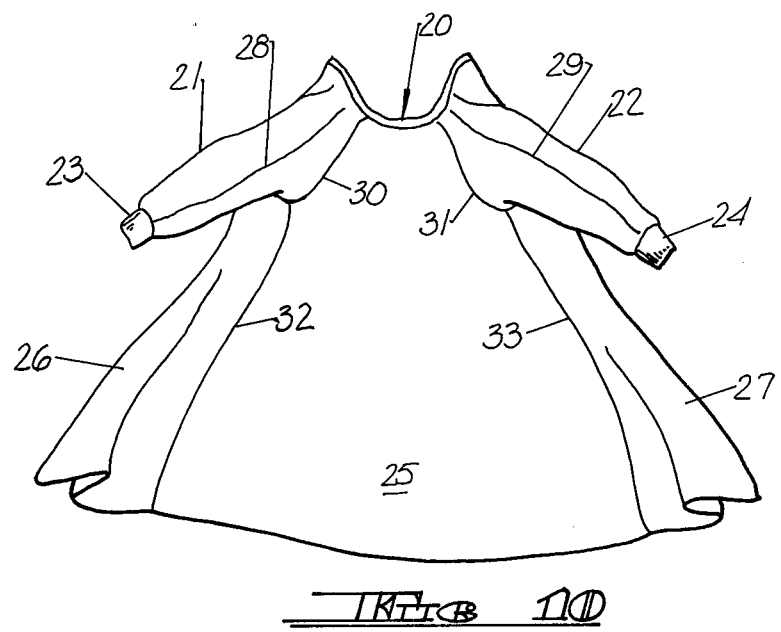
FIG. 10 is an elevational view of an exemplary surgical gown made of the fabric of the present invention.

It is also possible to vary the fabric's construction in different parts of drape 34 in much the same manner taught with respect to surgical gown 20 of FIG. 10. Thus, since the side panels 39 and 40 are likely to be subjected to less pressure by opposed surfaces and since large portions of them may well extend below the operating table, they could be made up of fabrics having fewer hydrophobic microfine fiber plies than the main body portion 35 of the drape.

Selected areas of drapes and gowns are conventionally reinforced by means of patches (of film, film laminates or the same material as used to make the drape or gown) which are adhesively affixed or otherwise attached to the drape or gown. Such patches may similarly be provided on drapes or gowns made of the fabric of the present invention. When an aperture film is used as a cover ply in the fabric of the present invention, areas of the film may be non-apertured to uniquely achieve the equivalent of such a patch without adding additional material, stiffness or cost to the gown or drape.

TEST PROCEDURES

The test procedures used to determine the unique properties of the composite nonwoven fabrics of the present invention and to engender the test results provided in the examples below are as follows:

TENSILE STRENGTH TEST

A 50.8 mm wide strip of the material for which tensile strength is to be determined is tested in an Instron Table Model TM with a tension load cell "C" (range 4.4–22.2 newtons). An initial jaw spacing of 50.8 mm is used together with a crosshead speed of 50.8 mm per minute. The tensile strength is reported as tensile to break in newtons per meter. A high value is desired.

TEAR STRENGTH TEST

Tear strength is determined using an Elmendorf Tearing Tester and ASTM Test Method D-1424, with the exception the sample is conditioned at 23°±1° C. and a relative humidity of 50±2% for 12 hours. The value is reported in grams and a high value is desired.

DRAPE TEST

Samples of the composite nonwoven fabric are evaluated after being conditioned at 23°±1° C. and 50±2% relative humidity for a minimum of 12 hours prior to testing. A 305 mm circular sample is placed and centered on a platform screen which surrounds and is substantially coplanar with the upper end of a 76 mm diameter circular pedistal. The platform screen is then dropped, causing the test sample to be supported only by the upper end of the pedestal. The draped form of the sample is then photographed. The photographed image of the draped sample is cut out and weighed. The ratio of the weight of the draped image to the weight of the undraped flat image is calculated and reported as the percent drape. A material having complete rigidity, with zero drapeability, would equal the original picture of the test sample in area and would have 100% drape. A material completely flexible, so that it draped vertically, would equal the picture of the supporting pedestal in size and would have 6% drape.

The calculation for percent drape is as follows:

$$\text{Percent Drape} = \frac{\text{wt. of draped image}}{\text{wt. of undraped image}} \times 100 \pm \text{correction factor}$$

Correction Factors:

| Number of Inward Folds | Correction Factor |
|---|---|
| 2 | + 7.0% |
| 3 | + 4.0% |
| 4 | + 0.0% |
| 5 | − 4.0% |

A low percent drape value is desired.

AIR PERMEABILITY TEST

The test for air permeability of the composite nonwoven fabrics conforms to the ASTM Test Method D-737, with the exception that the material to be tested is conditioned at 23°±1° C. and 50±2% relative humidity for a minimum of 12 hours prior to testing. The air permeability is reported as cubic millimeters per second per square millimeter at 12.7 mm $H_2O$ differential pressure. A high volume is desired.

LIQUID COLUMN STRIKETHROUGH RESISTANCE TEST

The liquid strikethrough resistance test is a method for determining the water pressure in millimeters of water at which water penetrates a repellent nonwoven fabric material at a specified fill rate and with the water and nonwoven fabric at a specified temperature.

The strikethrough tester comprises a vertically mounted clear plastic tube with an inside diameter of 50.8±1.6 mm with a flange on the bottom of the tube with rubber gaskets to hold the samples. Each sample consists of at least five individual test specimens cut to 90 mm by 90 mm.

Each test specimen is appropriately affixed to the bottom of the tube. Water is introduced into the tube at a filling rate of 6.7 cc per second giving a rate increase of water pressure of 3.3 mm of water per second. Both the water and the nonwoven fabric are conditioned to 23°±1° C. When the first drop of water penetrates the sample specimen, the column height is read for that specimen in millimeters of water. The liquid column strikethrough resistance value for each sample is an average of the values of the 5 specimens for that sample. A high value is desired.

BACTERIA STRIKETHROUGH RESISTANCE TEST

The nonwoven fabric to be tested is placed on a glass surface which has been covered with a plastic film. A small amount (less than 0.5 cc) of trypticase soy broth, contaminated with *Serratia marcescens*, is placed on top of the nonwoven fabric. A weight with a base of known cross-sectional area is gently placed on the broth on the fabric sample such that the broth wets the entire bottom surface of the weight. After 10 minutes the fabric sample and the weight are removed and the plastic film is cultured with a RODAC plate. The RODAC plate is incubated for from 24 to 48 hours. A bright orange-red mucoid growth indicates *Serratia marcescens* strikethrough. Any other growth can be interpreted as stray combination, some of which is expected since the samples tested are non-sterile. A positive control of the trypticase soy broth should be run with each set of samples to insure viability of the broth. The test is repeated with different weights until strikethrough occurs. The test is reported as the maximum pressure (kilonewtons/m$^2$) at which no *Serratia marcescens* occurred. Again a high value is desired.

WET ABRASION RESISTANCE TEST

Samples of fabric to be tested are cut into 150 mm×150 mm squares with a 12.7 mm diameter hole cut in the center. Each sample is placed in a weighing bottle and dried in an oven at 110° C. for 2 hours. The temperature and drying time may be adjusted for different types of fabrics. After removing the samples from the oven, they are placed in a dessicator and are allowed to cool to room temperature (approximately 1 hour).

The samples are then weighed to the nearest 0.0001 gram. Each sample is then placed on a Taber abraser-Research Model and the weight is set to a 125 gram load per wheel. CS-8 wheels are used. Two cubic centimeters of water are put on the sample and the wheels via pipette. The abraser is run the number of cyles desired, normally two hundred. The wheels are then lifted and the sample is brushed, making sure that all non-attached particles are removed. The particles which are loosely attached to the fabric remain. The wheels and table are dried and brushed to remove any clinging particles. Each sample is again placed in a weighing bottle and completely dried in an oven (the time and temperature being adjusted according to the fabric being tested). After each sample is removed from the oven and cooled to room temperature, it is again weighed and recorded, and the weight loss in milligrams is computed. A low number is desired.

REPEATED PRESSURE LIQUID STRIKETHROUGH RESISTANCE TEST

Samples to be tested are cut into squares approximately 130 mm on a side with a 10 mm diameter hole cut in the center. A circle of 90 mm diameter white filter paper (Whatman 40 is suitable) with a 10 mm diameter center hole, is placed in the turn table of a Taber Research Model Abraser. The fabric sample is secured in place on the abraser over the filter paper. With the counterweight set for a load of 125 grams per wheel, the wheels (CS-8 grade) are lowered gently onto the sample. One cubic centimeter of dyed water is pipetted onto the sample in front of the right wheel. The abraser is switched on for 5 cycles and then stopped. The wheels are lifted and the filter paper under the sample is then carefully examined for color, indicating strikethrough. If no strikethrough is evident, the abraser is run for 5 more cycles and the sample is checked again. This is repeated until strikethrough is noted or until 200 cycles are reached. Three replicates are averaged and the result reported is the number of cycles reached before strikethrough occurs. A high result is desired.

EXAMPLES

The following is a series of examples as described below. Each example was tested for basis weight, air permeability, liquid column strikethrough, bacteria stirkethrough, drape, Elmendorf tear, tensile strength, abrasion resistance and repeated pressure liquid strikethrough. The results of these tests are set forth in Tables I, II and III.

EXAMPLE I

A three ply composite, nonwoven fabric was made utilizing blue apertured polyethylene film as generally described in the above mentioned U.S. Pat. No. 3,929,135. The apertured film had an initial film thickness before aperturing of 0.03 mm. Two microfine fibers webs were used. These webs were melt blown polypropylene with an average fiber diameter of about 3 microns, a basis weight of about 15.5 g/m$^2$ and an initial density of about 0.08 g/cc.

A cover ply of the apertured film, oriented with the cones extending away from the fabric structure, and one web of polypropylene microfine fibers were laid together without bonding. A second microfine fiber layer was heat embossed to stabilize its surface against abrasion, using a broken linen pattern roll against a rubber back-up roll. The embossing roll temperature was 113° C. The nip pressure was 20.2 kilonewtons/m and the web speed was 0.08 m/sec. The density of the microfine fiber web after surface stabilization was about 0.10 g/cc. This stabilized microfine fiber web was laid on the structure against the first microfine fiber web with no bonding.

EXAMPLE II

A four ply, composite, nonwoven fabric was made, which was identical to the fabric of Example 1 with the exception that a fourth ply of spunbonded polypropylene sold by Crown Zellerbach Corporation of Camas, Wash., under the mark "Fibertex" was laid between the two microfine fiber webs. The spunbonded polypropylene web served as a strength ply and had a basis weight of about 17 g/m$^2$. The process conditions used to heat stabilize the outermost microfine fiber web were changed to an embossing roll temperature of 96° C., and a web speed of 0.1 m/sec.

EXAMPLE III

Another four ply, composite, nonwoven fabric was made. This fabric was identical to that of Example I except that there was no heat stabilization of the second microfine fiber web and a second apertured film was placed over the second microfine fiber web to form a second cover ply. The cones of both apertured film plies pointed outward, away from the center of the fabric.

EXAMPLE IV

Another four ply, composite, nonwoven fabric was made utilizing the following materials:

(a) a blue apertured film identical to that described with respect to Example I.

(b) a polypropylene microfine fiber web made by Riegel Products Corporation, Milford, N.J. under the mark "Polyweb" and having a basis weight of 15 g/m², an average fiber diameter of 3.2 microns and a density of 0.07 g/cc.

(c) a rayon carded web sold by Irving Textile Products, Inc. of Atglen, Pa., under mark "Context" and having a basis weight of 17 g/m².

(d) an acrylic latex emulsion sold by the Celanese Corporation of New York, N.Y., under the mark "Celca Cril 10645".

A 50% solid solution of acrylic latex was hand sprayed onto a microfine fiber web at about 1 to 2 grams solids/m² application rate. Blue apertured film, with its cones extending away from the microfine fiber web was adhered thereto by passing the film and the microfine fiber web through a set of nip rolls under less than 45 newtons/m pressure. The adhesive was air dried. In a similar fashion a rayon carded web was adhered to another microfine fiber web. These two-ply laminates were thereafter laid together with the microfine fiber webs adjacent each other.

EXAMPLE V

In this example the materials were identical to those described in Example IV. A two-ply laminate of an apertured film and a microfine fiber web was prepared as described, utilizing the acrylic latex emulsion. This two-ply laminate was laid together with two more microfine fiber webs and a carded rayon web such that the three microfine fiber webs were adjacent each other and covered on either side by the apertured film and the rayon carded web.

EXAMPLE VI

In this example a five-ply, composite, nonwoven web was prepared. The fabric was prepared utilizing the blue apertured film described in Example I, two polypropylene microfine fiber webs of the type described in Example I, a 17 g/m² spunbonded polypropylene web of the type described in Example II and a 17 g/m² carded rayon web of the type described in Example IV. All five of these webs were laid together without bonding in the following order: apertured film (cones directed outwardly of the fabric), a microfine fiber web, the spunbonded polypropylene web, a second microfine fiber web and the carded rayon web.

EXAMPLE VII

This example comprised a three-ply, composite, nonwoven fabric identical to that of Example I with the exception that the apertured film cover ply was replaced by a cover ply of spunbonded rayon produced by Asahi Chemical Industries, Limited, Osaka, Japan, under the mark "Bemliese" grade GS-302. The basis weight of the spunbonded rayon cover ply was about 30 g/m².

EXAMPLE VIII

Example VIII comprised a commercially available flashspun polyolefin nonwoven fabric sold by E. I. Dupont de Nemours, Wilmington, Del., under the mark "Tyvek", grade 1444S.

EXAMPLE IX

This example comprised a nonwoven fabric in the form of a scrim reinforced tissue fabric taken from a commercially available surgical gown pack such as is manufactured by the Convertors Division of The American Hospital Supply Corporation of Evanston, Ill. under the mark "Shield". The material has four tissue plies and a nylon scrim having a spacing of 2.1 mm × 5.1 mm and located between the second and third tissue plies.

EXAMPLE X

The nonwoven fabric of this example comprised a hydraulically entangled polyester and wood pulp fabric. The sample was taken from a commercially available surgical gown pack manufactured by the Surgikos Division of Johnson & Johnson, of New Brunswick, N.J., under the mark "Barrier".

EXAMPLE XI

The fabric of Example XI comprised a spunbonded polyester reinforced tissue laminate for surgical gowns made by the process set forth in the above mentioned copending application Ser. No. 741,640.

EXAMPLE XII

The fabric of this example comprised an unwaterproofed reusable cotton muslin drape/gown material sold by Kansas City White Goods Manufacturing Company, Kansas City, Mo., under the designation Type 140 Muslin Sheeting. The fabric was new and was tested without any laundering.

TABLE I

| Example No. | Basis Weight (g/m²) | Air Permeability at 12.7 mm H₂O (mm³/sec-mm²) | Liquid Column Strikethrough (mm H₂O) | | Bacteria Strikethrough Resistance at 10 min (kilonewtons/m²) | |
|---|---|---|---|---|---|---|
| | | | Side 1 | Side 2 | Side 1 | Side 2 |
| 1 | 65 | 183 | 673 | 660 | 27.6+ | 27.6+ |
| 2 | 79 | 168 | 605 | 561 | 27.6+ | 27.6+ |
| 3 | 80 | 208 | 511 | | 27.6+ | |
| 4 | 83 | 315 | 292 | 318 | 27.6+ | 27.6+ |
| 5 | 96 | 254 | 437 | 411 | 27.6+ | 27.6+ |
| 6 | 98 | 173 | 475 | 422 | 27.6+ | 27.6+ |
| 7 | 64 | 269 | 569 | 599 | 27.6+ | 27.6+ |
| 8 | 44 | 5 | 1207 | | 13.8 | |
| 9 | 92 | 107 | 191 | | 3.5 | |
| 10 | 68 | 467 | 185 | | 2.1 | |
| 11 | 75 | 224 | 188 | | 2.1 | |
| 12 | 171 | 152 | <10 | | 0 | |

TABLE II

| Example No. | Repeated Pressure Strikethrough (cycles) | | Drape (%) | Abrasion Resistance at 200 cycles (mg lost) | |
|---|---|---|---|---|---|
| | Side 1 | Side 2 | | Side 1 | Side 2 |
| 1 | 200+ | 5 | 24 | 5 | 5 |
| 2 | 200+ | 200+ | 23 | 5 | 5 |
| 3 | 200+ | | 18 | 5 | 5 |
| 4 | 190 | 18 | 48 | 5 | 2 |
| 5 | 200+ | 20 | 41 | 5 | 3 |
| 6 | 200+ | 38 | 28 | 5 | 3 |
| 7 | 45 | 23 | 25 | 2 | 3 |
| 8 | 20 | | 45 | 2 | |
| 9 | <5 | | 46 | >10 | |
| 10 | <5 | | 29 | >10 | |
| 11 | <5 | | 39 | >10 | |
| 12 | <1 | | 24 | 6 | |

TABLE III

| Example No. | Tensile (newtons/m) | | Elmendorf Tear (grams) | |
|---|---|---|---|---|
| | MD | CD | MD | CD |
| 1 | 613 | 508 | 240 | 144 |
| 2 | 684 | 754 | 784 | 715 |
| 3 | 701 | 859 | 480 | 176 |
| 4 | 1472 | 421 | 126 | 333 |
| 5 | 1542 | 491 | 125 | 376 |
| 6 | 1349 | 613 | 789 | 901 |
| 7 | 824 | 543 | 576 | 869 |
| 8 | 2015 | 2200 | 939 | 1104 |
| 9 | 1455 | 894 | 401 | 416 |
| 10 | 1665 | 631 | 676 | 669 |
| 11 | 1297 | 1052 | 591 | 700 |
| 12 | — | — | 1216 | 1339 |

In the column of Table I which sets forth the bacteria strikethrough results, the "+" sign indicates that the fabric did not fail within the 10 minute time period at the indicated pressure. Examples 1 through 7 are examples of composite nonwoven fabrics made in accordance with the teachings of the present invention. For these Examples "side 1" has been designated to indicate the side most likely to be outermost on a gown or uppermost on a drape, thus being the side more likely to have liquid loadings and/or abrasion in use. Specifically, in Examples 1, 2 and 4 through 6, side 1 is the apertured film side, and in Example 7, side 1 is the spunbonded rayon side. Example 3 and the prior art Examples 8 through 12 have essentially identical surfaces and their data have been shown only as side 1. Basis weight, air permeability, drape, tensile and tear do not depend upon the surface differences and have been shown without reference to side for all Examples.

A comparison of the air permeability, liquid column strikethrough and bacteria strikethrough columns of Table I will show that the fabrics of the present invention possess a liquid and bacteria strikethrough resistance/air permeability relationship not possessed by the prior art fabrics. A comparison of the air permeability (Table I) and repeated strikethrough (Table II) from the outer or upper side (side 1) of the fabrics of the present invention will show the same unique strikethrough/air permeability relationship and will also show the importance of apertured film as a cover ply. It will be noted that the repeated pressure strikethrough data from the inner or underside (side 2) of the fabrics of the present invention are better than all prior art Examples with the exception of Example 8 which is less desirable as a surgical fabric in that it possesses essentially no air permeability.

The drape column of Table II reveals that the fabrics of the present invention demonstrate excellent drape characteristics approaching that of cloth and generally better than most nonwoven prior art. It will be noted from Table III that the fabrics of the present invention demonstrate an abrasion resistance which compares favorably with or is superior to the majority of the prior art fabrics.

Modifications may be made in the invention without departing from the spirit of it.

The embodiments of the invention in which an exclusive property or privilege is claimed are defined as follows.

1. A composite nonwoven fabric comprising at least two adjacent hydrophobic plies of microfine fibers having a fiber diameter of up to 10 microns, each of said microfine fiber plies having a basis weight of at least about 10 g/m$^2$ and an initial density of up to about 0.15 g/cc, and one air permeable, nonwoven cover ply.

2. The structure claimed in claim 1 including a second air permeable, nonwoven cover ply.

3. The structure claimed in claim 1 wherein said at least two microfine fiber plies each have a basis weight of from about 15 g/m$^2$ to about 30 g/m$^2$.

4. The structure claimed in claim 1 including up to 5 of said adjacent microfine fiber plies.

5. The structure claimed in claim 1 wherein said at least two microfine fiber plies each comprise a meltblown web made from at least one material chosen from the class consisting of nylon, polyester and polypropylene.

6. The structure claimed in claim 1 wherein said cover ply comprises a liquid impervious film having a plurality of tapered capillaries formed therein.

7. The structure claimed in claim 1 wherein said cover ply comprises a spunbonded web made from at least one material chosen from the class consisting of rayon, polyester, polypropylene and nylon and having a filament diameter of up to 40 microns and a basis weight of up to about 34 g/m$^2$.

8. The structure claimed in claim 1 wherein said cover ply comprises a web of discontinuous fibers of a length of at least about 10 mm and made from at least one material chosen from the class consisting of cellulose fibers, rayon fibers, polypropylene fibers, polyester fibers and nylon fibers, said cover ply having a basis weight of up to about 34 g/m$^2$.

9. The structure claimed in claim 1 wherein said cover ply is hydrophobic.

10. The structure claimed in claim 1 wherein said cover ply is hydrophilic.

11. The structure claimed in claim 1 including a nonwoven strength ply located within said structure between said cover ply and the adjacent one of said microfine fiber plies, said strength ply being hydrophobic and having a basis weight of up to about 34 g/m$^2$, said strength ply comprising a spunbonded web made from at least one material chosen from the class consisting of rayon, polyester, polypropylene and nylon and having a filament diameter of up to 40 microns.

12. The structure claimed in claim 1 including a nonwoven strength ply located within said structure between said cover ply and the adjacent one of said microfine fiber plies, said strength ply being hydrophobic and having a basis weight of up to about 34 g/m$^2$, said strength ply comprising a web of discontinuous fibers of a length of at least about 10 mm and made from at least one material chosen from the class consisting of cellulose fibers, rayon fibers, polypropylene fibers, polyester fibers and nylon fibers.

13. The structure claimed in claim 1 wherein one of said at least two microfine fiber plies comprises an outermost ply of said composite nonwoven fabric, said outermost microfine fiber ply being surface stabilized.

14. The structure claimed in claim 1 wherein said composite nonwoven fabric has an air permeability of at least 150 mm$^3$/sec-mm$^2$, a liquid column strikethrough resistance of at least 250 mm, and a bacteria strikethrough resistance of at least 20 kilonewtons/m$^2$ and each of said microfine fiber plies has a density of up to 0.1 g/cc.

15. The structure claimed in claim 1 wherein said at least two microfine fiber plies are melt-blown polypropylene webs and said cover ply comprises a hydrophilic web of spunbonded rayon, said cover ply having a basis weight of up to about 34 g/m$^2$, the exposed one of said melt-blown webs being surface stabilized.

16. The structure claimed in claim 1 wherein said cover ply and said at least two microfine fiber plies are joined together by spot bonds.

17. The structure claimed in claim 1 wherein selected adjacent ones of said cover ply and said at least two microfine fiber plies are joined together by spot bonds.

18. The structure claimed in claim 2 wherein said at least two microfine fiber plies each have a basis weight of from about 15 g/m$^2$ to about 30 g/m$^2$.

19. The structure claimed in claim 2 including up to 5 of said adjacent microfine fiber plies.

20. The structure claimed in claim 2 wherein said at least two microfine fiber plies each comprise a melt-blown web made from at least one material chosen from the class consisting of nylon, polyester and polypropylene.

21. The structure claimed in claim 2 wherein at least one of said cover plies comprises a liquid impervious film having a plurality of tapered capillaries formed therein.

22. The structure claimed in claim 2 wherein at least one of said cover plies comprises a spunbonded web made from at least one material chosen from the class consisting of rayon, polyester, polypropylene and nylon and having a filament diameter of up to 40 microns and a basis weight of up to about 34 g/m$^2$.

23. The structure claimed in claim 2 wherein at least one of said cover plies comprises a web of discontinuous fibers of a length of at least about 10 mm and made from at least one material chosen from the class consisting of cellulose fibers, rayon fibers, polypropylene fibers, polyester fibers and nylon fibers, said cover ply having a basis weight of up to about 34 g/m$^2$.

24. The structure claimed in claim 2 wherein said cover plies are hydrophobic.

25. The structure claimed in claim 2 wherein one of said cover plies is hydrophobic and the other of said cover plies is hydrophilic.

26. The structure claimed in claim 2 including a nonwoven strength ply located within said structure between one of said cover plies and the adjacent one of said microfine fiber plies, said strength ply being hydrophobic and having a basis weight of up to about 34 g/m$^2$, said strength ply comprising a spunbonded web made from at least one material chosen from the class consisting of rayon, polyester, polypropylene and nylon and having a filament diameter of up to 40 microns.

27. The structure claimed in claim 2 including a nonwoven strength ply located within said structure between one of said cover plies and the adjacent one of said microfine fiber plies, said strength ply being hydrophobic and having a basis weight of up to about 34 g/m$^2$, said strength ply comprising a web of discontinuous fibers of a length of at least about 10 mm and made from at least one material chosen from the class consisting of cellulose fibers, rayon fibers, polypropylene fibers, polyester fibers and nylon fibers.

28. The structure claimed in claim 2 including 3 microfine fiber plies of melt-blown polypropylene, one of said cover plies comprising a liquid impervious film having a plurality of tapered capillaries formed therein, the other of said cover plies comprising a hydrophilic web of discontinuous rayon fibers of a length of at least 10 mm, said last mentioned cover ply having a basis weight of up to about 34 g/m$^2$.

29. The structure claimed in claim 2 wherein said microfine fiber plies comprise 2 webs of melt-blown polypropylene, one of said cover plies comprising a liquid impervious film having a plurality of tapered capillaries formed therein, the other of said cover plies comprising a hydrophilic web of discontinuous rayon fibers of a length of at least 10 mm, said last mentioned cover ply having a basis weight of up to about 34 g/m$^2$.

30. The structure claimed in claim 2 wherein all of said plies thereof are joined together by spot bonds.

31. The structure claimed in claim 2 wherein selected adjacent ones of said plies are joined together by spot bonds.

32. The structure claimed in claim 2 wherein said composite nonwoven fabric has an air permeability of at least 150 mm$^3$/sec-mm$^2$, a liquid column strikethrough resistance of at least 250 mm, and a bacteria strikethrough resistance of at least 20 kilonewtons/m$^2$ and each of said microfine fiber plies has a density of up to 0.1 g/cc.

33. The structure claimed in claim 1 including a nonwoven strength ply located within said structure between said at least two adjacent microfine fiber plies, said strength ply being hydrophobic and having a basis weight of up to about 34 g/m$^2$, said strength ply comprising a spunbonded web made from at least one material chosen from the class consisting of rayon, polyester, polypropylene and nylon and having a filament diameter of up to 40 microns.

34. The structure claimed in claim 1 including a nonwoven strength ply located within said structure between said at least two adjacent microfine fiber plies, said strength ply being hydrophobic and having a basis weight of up to about 34 g/m$^2$, said strength ply comprising a web of discontinuous fibers of a length of at least about 10 mm and made from at least one material chosen from the class consisting of cellulose fibers, rayon fibers, polypropylene fibers, polyester fibers and nylon fibers.

35. The structure claimed in claim 2 including a nonwoven strength ply lcoated within said structure between said at least two adjacent microfine fiber plies, said strength ply being hydrophobic and having a basis weight of up to about 34 g/m$^2$, said strength ply comprising a spunbonded web made from at least one material chosen from the class consisting of rayon, polyester, polypropylene and nylon and having a filament diameter of up to 40 microns.

36. The structure claimed in claim 2 including a nonwoven strength ply located within said structure between said at least two adjacent microfine fiber plies, said strength ply being hydrophobic and having a basis weight of up to about 34 g/m², said strength ply comprising a web of discontinuous fibers of a length of at least about 10 mm and made from at least one material chosen from the class consisting of cellulose fibers, rayon fibers, polypropylene fibers polyester fibers and nylon fibers.

* * * * *

UNITED STATES PATENT AND TRADEMARK OFFICE
CERTIFICATE OF CORRECTION

PATENT NO. : 4,196,245
DATED : April 1, 1980
INVENTOR(S) : Richard P. Kitson, Richard L. Gilbert, Jr. & Joseph Israel It is certified that error appears in the above-identified patent and that said Letters Patent are hereby corrected as shown below:

On the title page of the patent:

Assignee: Buckeye Cellulos Corporation
Memphis, Tenn.

Should read:

Assignee: Buckeye Cellulose Corporation,
Cincinnati, Ohio

Signed and Sealed this

Twenty-third Day of September 1980

[SEAL]

Attest:

SIDNEY A. DIAMOND

Attesting Officer

Commissioner of Patents and Trademarks